(12) United States Patent
Ho et al.

(10) Patent No.: US 6,596,306 B1
(45) Date of Patent: Jul. 22, 2003

(54) DRUG DELIVERY SYSTEM:FORMULATION FOR FAT-SOLUBLE DRUGS

(76) Inventors: David Ho Sue San Ho, 121, Jln Kuala Kangsar, 30010 Ipoh, Perak (MY); Yuen Kah Hay Yuen, No. 7, Lorong Batu Uban5, Taman Century, 11700 Gelugor, Penang (MY); Yap Siew Ping Yap, 35, Halaman Free School, 11600 Penang (MY)

( * ) Notice: Subject to any disclaimer, the term of this patent is extended or adjusted under 35 U.S.C. 154(b) by 0 days.

(21) Appl. No.: 09/612,434

(22) Filed: Jul. 7, 2000

(51) Int. Cl.[7] .................. A61K 9/127; A61K 31/355; A61K 31/19; A61K 31/59
(52) U.S. Cl. ................. 424/450; 514/458; 514/167; 514/568
(58) Field of Search ................. 514/458, 167; 424/450

(56) References Cited

U.S. PATENT DOCUMENTS

| | | | | |
|---|---|---|---|---|
| 5,447,729 A | * | 9/1995 | Belenduik et al. | |
| 5,479,540 A | * | 12/1995 | Boudreau et al. | 385/14 |
| 5,750,142 A | * | 5/1998 | Friedman et al. | |
| 5,824,638 A | * | 10/1998 | Burnside et al. | |
| 5,858,330 A | * | 1/1999 | Boltri et al. | |
| 5,883,103 A | * | 3/1999 | Burnside et al. | |
| 5,897,876 A | * | 4/1999 | Rudnic et al. | |
| 6,267,985 B1 | * | 7/2001 | Chen et al. | 424/451 |
| 6,309,633 B1 | * | 10/2001 | Ekwuribe et al. | 424/85.1 |
| 6,451,339 B2 | * | 9/2002 | Patel et al. | 424/451 |
| 2002/0025337 A1 | * | 2/2002 | Illum et al. | 424/450 |

* cited by examiner

*Primary Examiner*—William R. A. Jarvis
*Assistant Examiner*—Vickie Kim
(74) *Attorney, Agent, or Firm*—David G. Oberdick; Chiara F. Orsini

(57) ABSTRACT

This invention relates to a novel formulation for fat-soluble drugs which self-emulsify in the presence of an aqueous medium with little agitation. More specifically, the invention is concerned with the formulation of a new dosage form for fat-soluble drugs in the form of a soft-gelatin capsule which forms emulsion instantly when the contents are released and mixed with gastrointestinal fluid. The formulation comprises a suitable mixture of drug with an appropriate oil and an appropriate surfactant system.

4 Claims, 6 Drawing Sheets

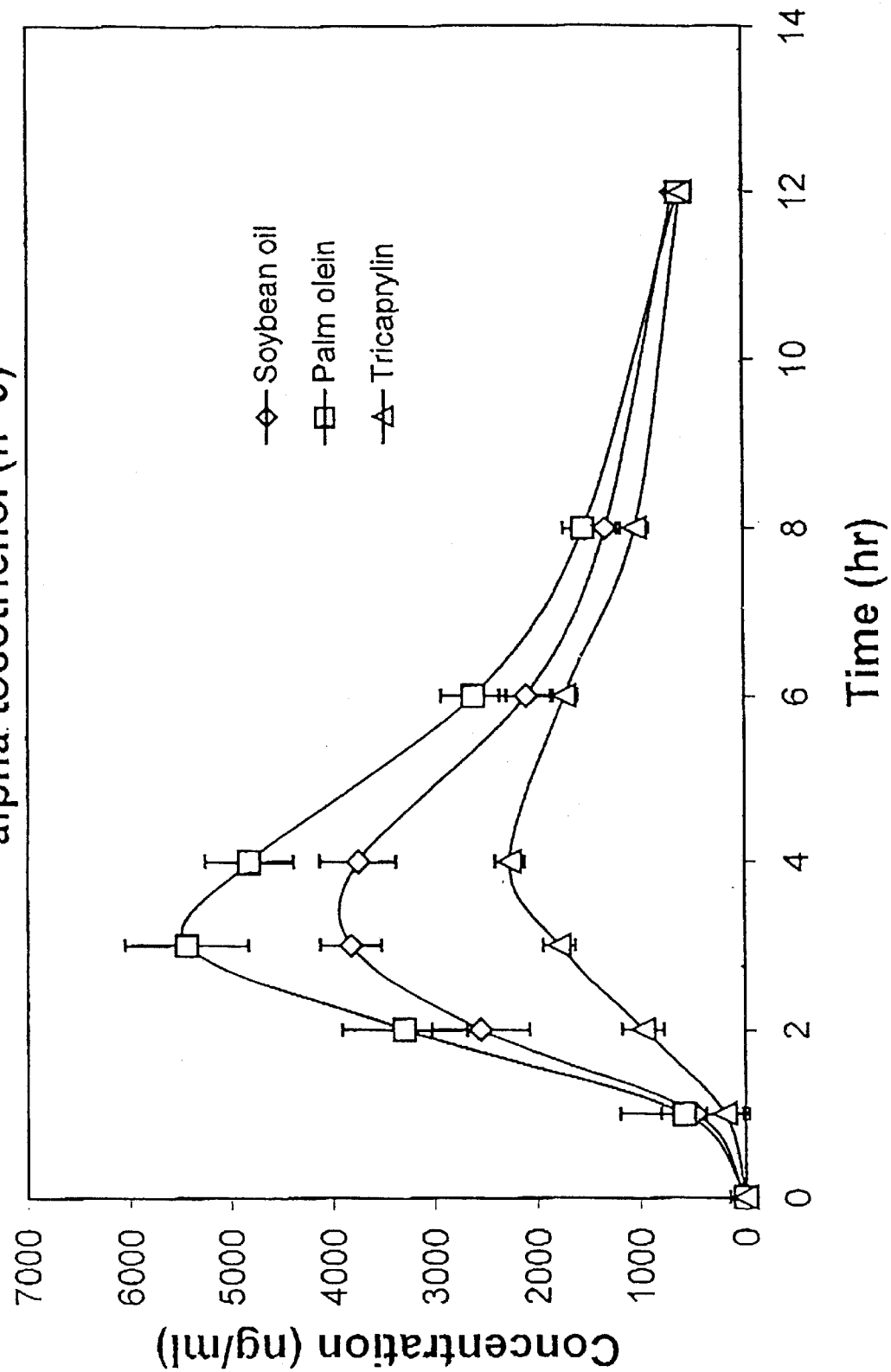

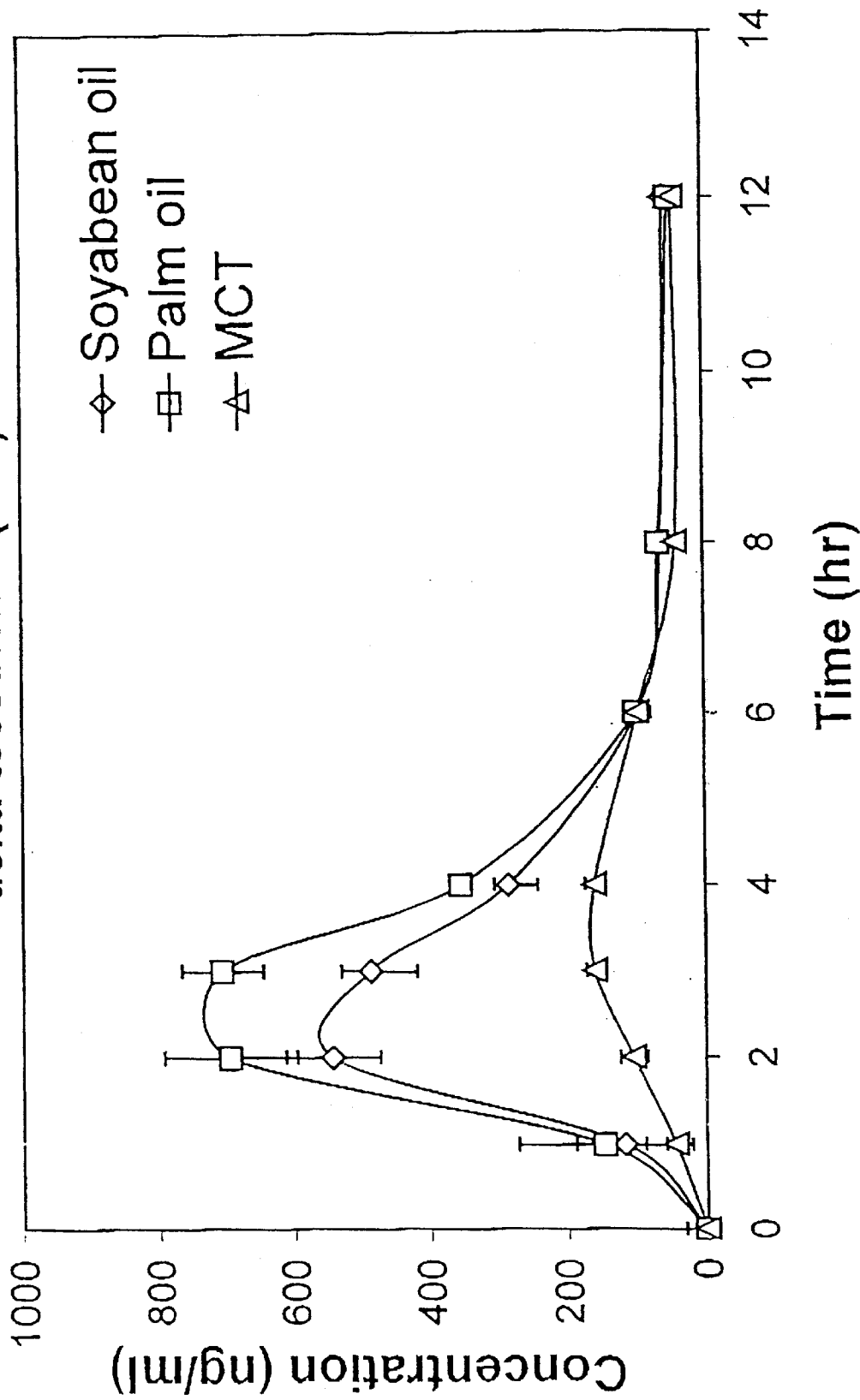
Fig. 1b Plasma concentration versus time profiles of delta-tocotrienol (n=9)

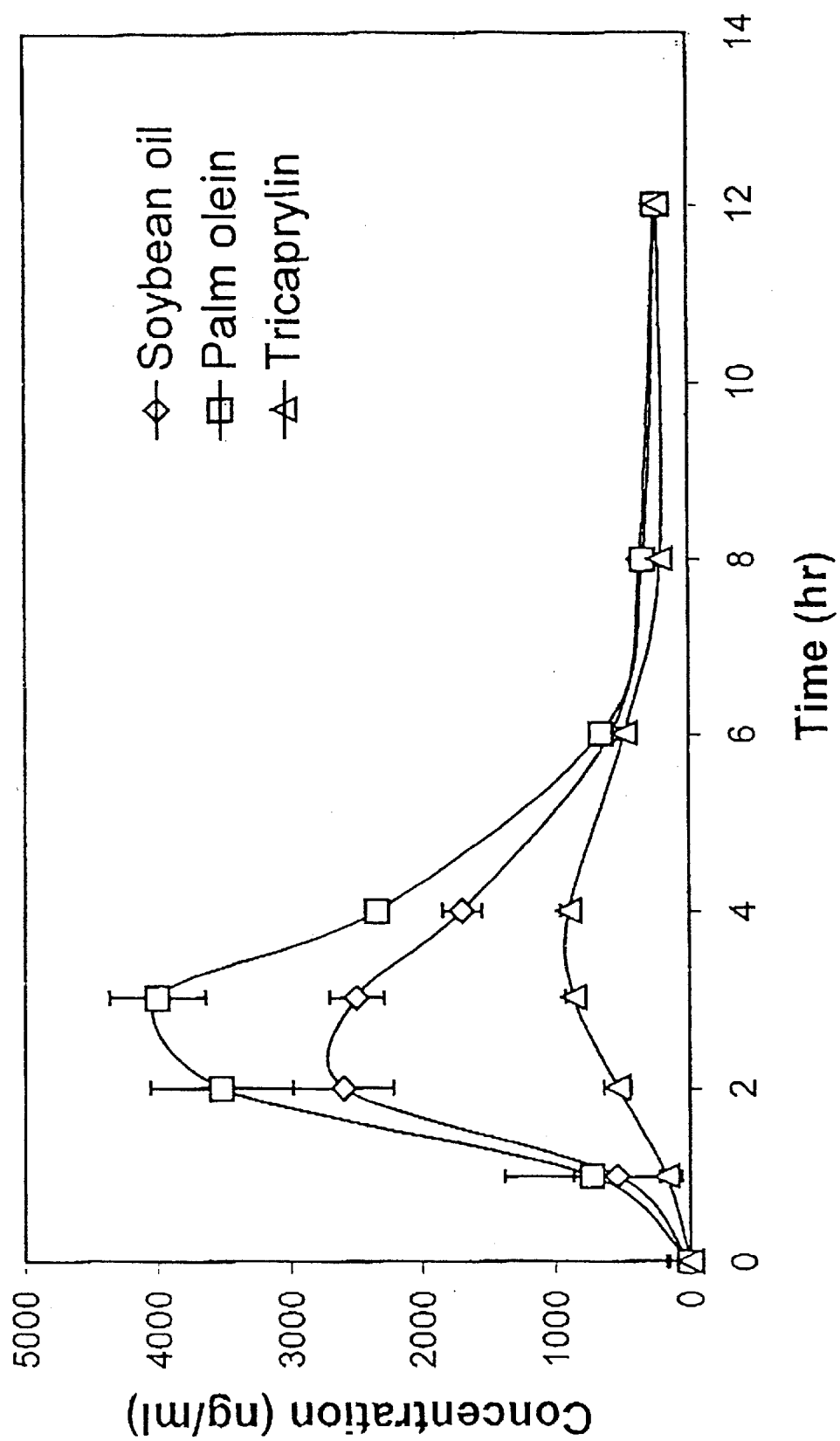

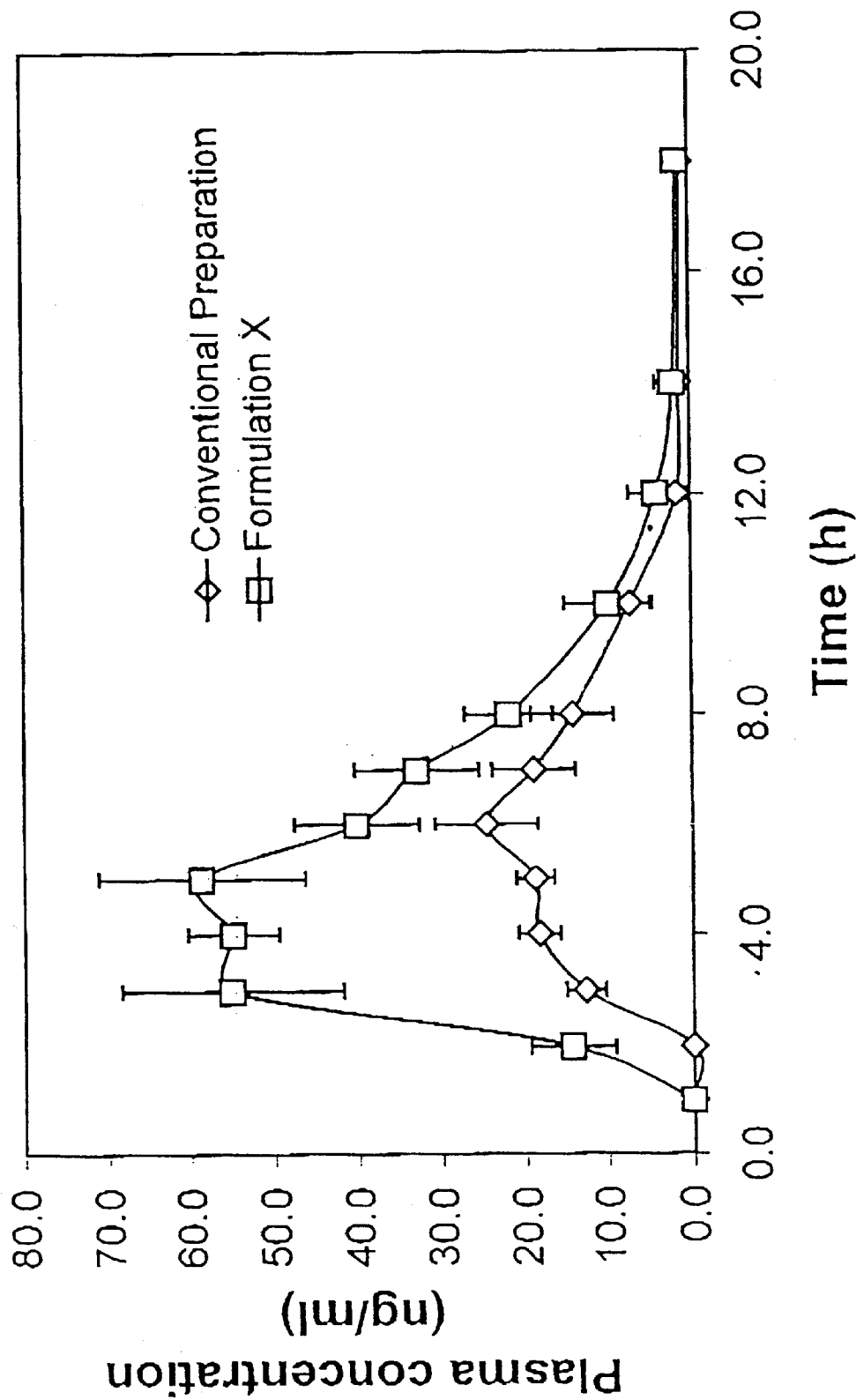

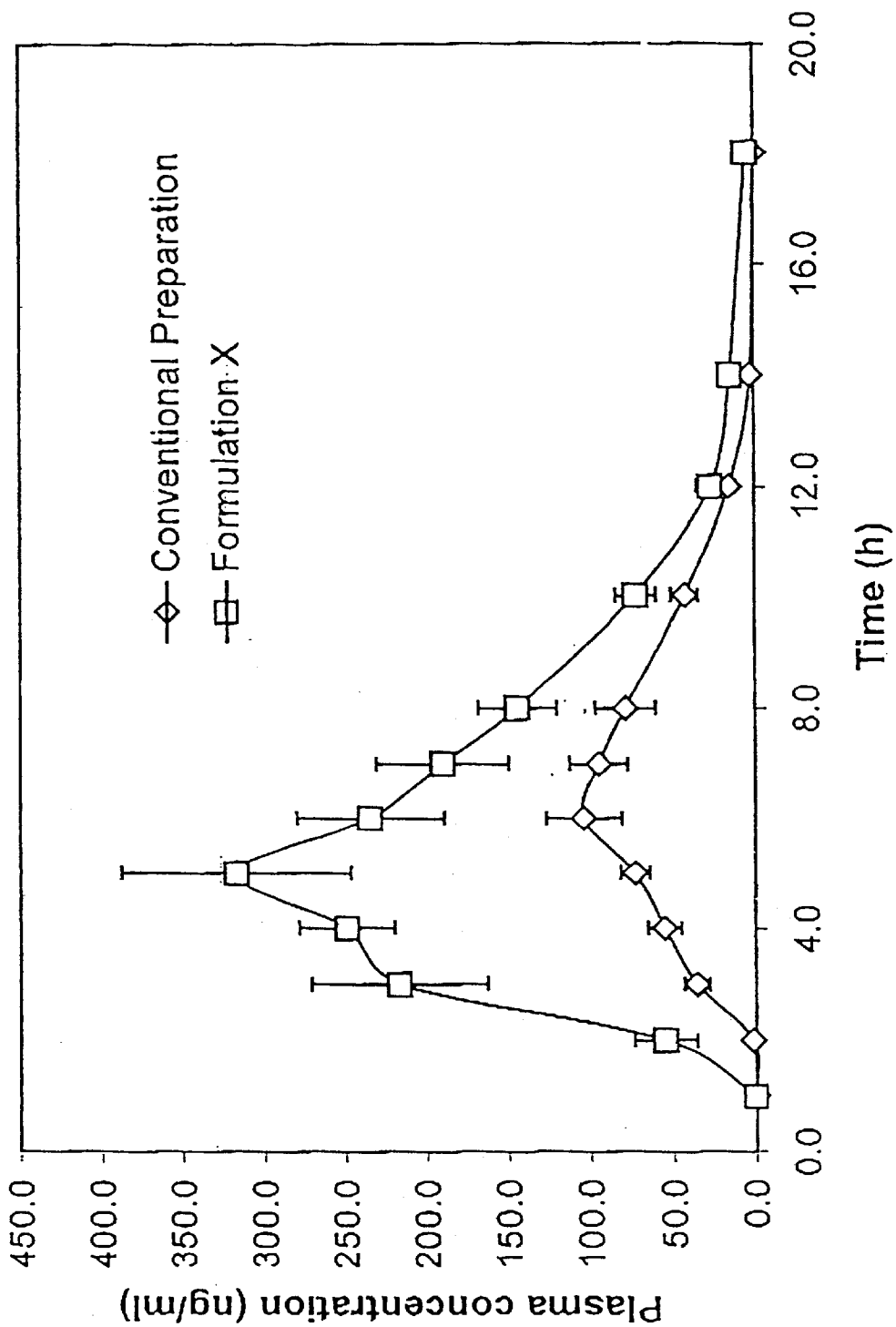
Fig. 2b Mean plasma gamma-tocotrienol versus time curves of the conventional preparation and Formulation X

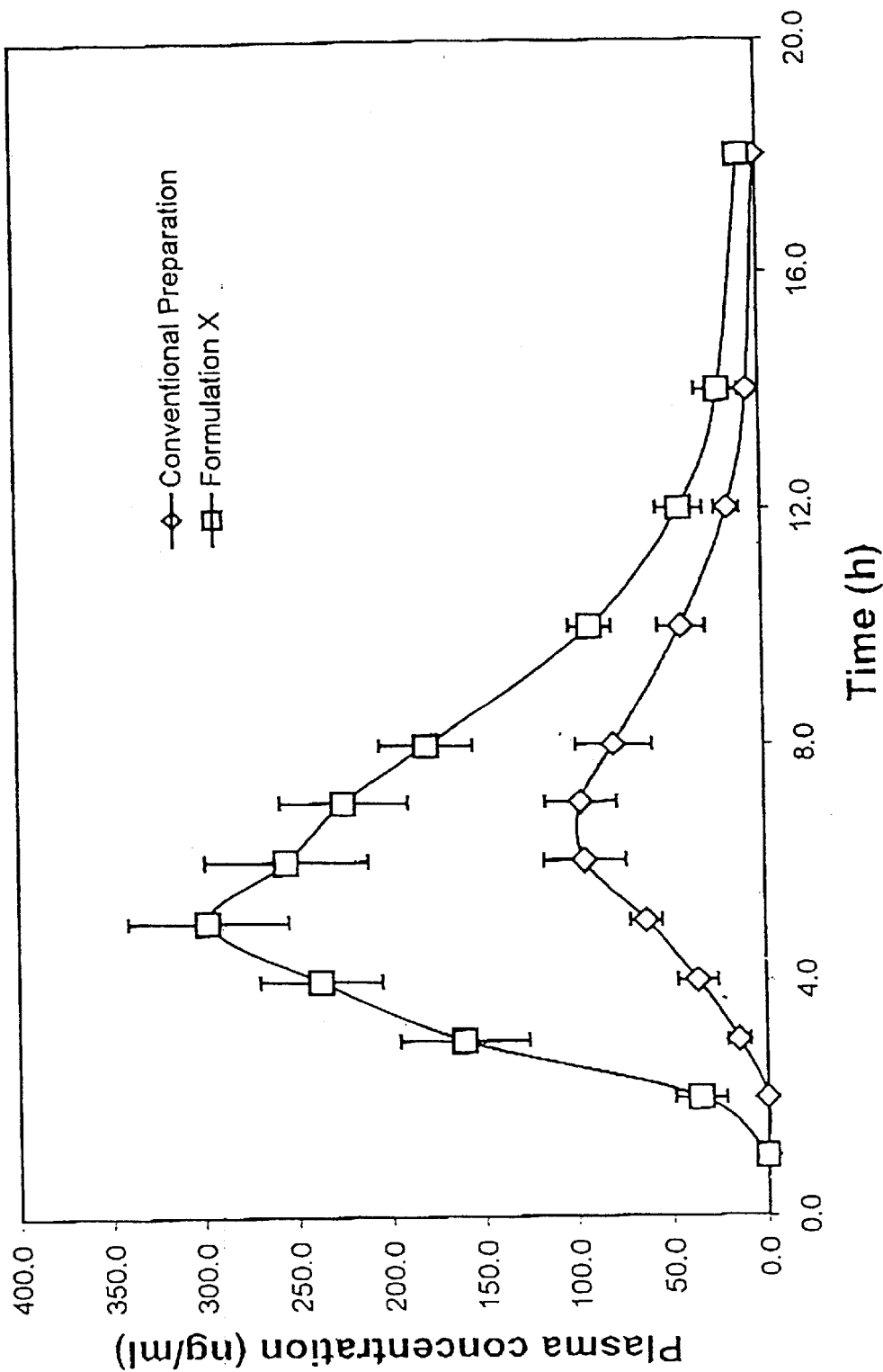
Fig. 2c Mean plasma alpha-tocotrienol versus time curves of the conventional preparation and Formulation X

DRUG DELIVERY SYSTEM:FORMULATION FOR FAT-SOLUBLE DRUGS

TECHNICAL FIELD OF THE INVENTION

This invention relates to a novel formulation for fat-soluble drugs (including tocotrienols, tocopherols, vitamin A, D and β-carotene) which self-emulsify in the presence of an aqueous medium with little agitation. More specifically, the invention is concerned with the formulation of a new dosage form for fat-soluble drugs in the form of a soft-gelatin capsule which forms emulsion instantly when the contents are released and mixed with our gastrointestinal fluid. Since emulsions are known to increase absorption of fat-soluble drugs, the dosage form thus provides higher and more consistent drug absorption. The success of the invention lies in its ability to self-emulsify in the gastrointestinal tract and comprised a suitable mixture of the drug with an appropriate oil and an appropriate surfactant system.

BACKGROUND OF THE INVENTION

Fat-soluble drugs such as tocotrienols and tocopherols are absorbed in the same pathway as other nonpolar lipids such as triglycerides and cholesterol (Kayden and Traber, 1993, J. Lipid Res., 34:343–358). Liver produces bile to emulsify the tocopherols incorporating them into micelles along with other fat-soluble compounds to facilitate absorption. Therefore, dietary fat, which promotes production of lipases and bile, is essential for absorption of vitamin E. However, if dietary fat is insufficient to stimulate adequate bile secretion, or bile secretion is affected by some pathological conditions such as biliary obstruction, then absorption of the fat-soluble drugs will be erratic and low. Also, it is known that absorption of fat-soluble drugs tend to be erratic and low when taken fasted or on an empty stomach.

Emulsions have been known to improve absorption of oil soluble drugs. However, conventional emulsions are not a preferred dosage form since they are bulky, have shorter shelf life due to stability problem and are less palatable. In recent years, there is a great interest in self-emulsifying drug delivery systems (SEDDS) due to the many advantages offered by these kind of systems which include enhanced bioavailability, improved reproducibility of plasma profiles and reduced inter- and intra-subject variability. SEDDS are formulated in the absence of water by mixing oil with one or more suitable non-ionic surfactants. Drugs, which have adequate solubility in the oil/surfactant blend, can be incorporated into the systems. Upon dilution or in vivo administration they form fine oil in water emulsions spontaneously with gentle agitation.

In the present studies it is discovered that the bioavailability of δ-, γ- and α-tocotrienols in palm olein and soybean oil mixtures were approximately 2.7, 2.8, 1.9 times and 2.2, 2.1, 1.6 times that of tocotrienols in medium chain triglyceride mixtures in rats respectively. This could be attributed to the long chain fatty acid of palm olein and soybean oil, which promote the absorption of tocotrienols into the lymph. A number of studies (Sieber et al, 1974, Xenobiotica 4, 265–284 and Palin et al, 1984, J. Pharm. Pharmacol. 36, 641–643) have shown that long chain fatty acids (>C14) (which are present in the palm oil and soybean oil), tend to increase absorption of oil soluble drug through the lymphatic system.

The present studies led to the discovery of a novel formulation by suitably blending palm olein or soybean oil with an appropriate surfactant mixture of Labrasol (caprylocaproyl macrogolglycerides) and Tween 80. The Labrasol to Tween 80 ratio was between 9:1 and 7:3. The above system could self-emulsify easily in water with gentle agitation (such as movement of stomach/small intestine). Therefore, the formulation need not be prepared like a usual emulsion, which is bulky and not palatable. Instead, the mixture is filled in a soft gelatin capsule. In stomach, the capsule wall dissolves and disintegrates and releases the contents, which will readily form an emulsion. Emulsions will give a bigger surface area for absorption and subsequently increased the absorption of fat-soluble drugs like tocotrienols. It was also demonstrated that the self-emulsifying system comprising the palm olein or soybean oil blended with the surfactant mixture could self-emulsify readily with water, when incorporated with fat soluble drugs including tocotrienols, tocopherols, vitamin A, vitamin D and β-carotene. In addition, the novel formulation could increase the absorption of δ-, γ- and α-tocotrienols by approximately 2 to 3 times that of the normal conventional soft gelatin capsule formulation when evaluated using twelve healthy human volunteers. The ratio of the surfactants to the oil and drug mixture was also demonstrated to be very important for enhanced drug absorption. For example, it was demonstrated that equal proportions of surfactant to the drug and oil mixture gave poor absorption whereas one part of surfactants to five parts of drug and oil mixture produced not only good self-emulsifying properties but also optionally enhanced drug absorption.

In conclusion, the studies had optimized three important formulation variables to achieve a superior product with enhanced bioavailability/absorption, namely (i) use of palm olein and soybean oil as the vehicle for fat-soluble drugs like tocotrienols, which help to enhance absorption;

(ii) addition of a suitable combination of Labrasol and Tween 80 into the drug/oil mixture to promote self-emulsification and thus help to further increase the absorption of tocotrienols; and (iii) a suitable combination of surfactant system (Labrasol and Tween 80) with the oil/drug mixture to optimize drug absorption.

SUMMARY OF THE INVENTION

Accordingly, it is the object of the present invention to provide a novel formulation for fat-soluble drugs that can self-emulsify in aqueous medium with little agitation.

This objective is accomplished by providing,

A pharmaceutical formulation for oral administration which comprises:

(i) a fat-soluble drug;

(ii) an appropriate oil; and (iii) an appropriate surfactant system;

the resulting formulation which self-emulsifies under gentle agitation in the presence of an aqueous medium.

According to the present invention, there is provided a new formulation of tocotrienols, in which the tocotrienols are incorporated into a palm olein-surfactant system to form a self-emulsifying system. This formulation is made into soft gelatin capsule and in stomach, the contents are released, resulting in the formation of emulsion and therefore increased absorption.

The formulation of tocotrienols in the present invention has an improved bioavailability when compared with the conventional preparation.

DETAILED DESCRIPTION OF THE INVENTION

Tocotrienols, as Tocomin® 50%, contains a minimum of 50.0% of phyto-tocotrienol/tocopherol complex, was obtained commercially from Carotech (Ipoh, Malaysia).

In the first part of the study, three different oil vehicles were compared concerning the influence of the different oils on the absorption of tocotrienols. The oil vehicles studied were as follows:

(i) palm olein (triglycerides of palmitic acid 46.5%, oleic acid 37.1% and linoleic acid 9.9%);

(ii) soybean oil (glycerides of linoleic acid 50–57%; linolenic acid 5–10%, oleic acid 17–26%; palmitic acid 9–13% and stearic acid 3–6%); and (iii) trycaprylin (not less than 95% are triglycerides of the saturated fatty acids octanoic (caprylic) acid and decanoic (capric) acid.

10% of Tocomin® 50% were then dissolved in these three oil vehicles and the same dose level (10 mg) were given to 9 rats in a 3 period, 3 sequence crossover study. The nine rats were randomly divided into 3 groups of 3 in each, and administered the preparations according to the schedule shown below:

| Group | Period | | |
|---|---|---|---|
| | I | II | III |
| 1 | Palm olein | Soybean oil | Tricaprylin |
| 2 | Tricaprylin | Palm olein | Soybean oil |
| 3 | Soybean oil | Tricaprylin | Palm olein |

The animals were fasted for 12-hr prior to, and for a 12-hr period subsequent to, the initiation of the absorption experiments. However, they were allowed free access to water throughout the experiment. The animals were subsequently placed in restraining cages, and approximately 0.5 ml blood samples were collected from the tail vein into heparinized tubes at 1, 2, 3, 4, 6, 8 and 12 hr, post-administration. The blood samples were then centrifuged for 10 min at 12800G, and 0.2–0.3ml aliquot of plasma obtained was transferred into a new Eppendorf tube. All plasma samples were immediately frozen at −20° C. until analysis.

Plasma $\alpha$-, $\delta$- and $\gamma$-tocotrienols were determined by high-performance liquid chromatography (HPLC) using a method reported by Yap et al, 1999, (Journal of Chromatography B, 735:279–283) with slight modification.

The mean plasma concentration versus time profiles of $\alpha$-, $\delta$- and $\gamma$-tocotrienols obtained with Tocomin® 50% in three oil bases, namely palm olein, soybean oil and medium chain triglyceride are shown in FIGS. 1a, 1b and 1c. It was apparent from the plots and the results that the absorption of $\alpha$-, $\delta$- and $\gamma$-tocotrienols from Tocomin® 50% in palm olein were the highest follow by Tocomin® 50% in soybean oil and Tocomin® 50% in Tricaprylin gave the lowest absorption. The difference in bioavailability of the three homologues of tocotrienols for the different oil vehicles was statistically significant.

From the 90% confidence interval for the ratio of the logarithmic transformed $AUC_{0-}$ values, it appeared that Tocomin® 50% in palm olein and soybean oil achieved a higher extent of absorption compared to Tricaprylin, which was about 2.7 times, 2.8 times 1.9 times and 2.2, 2.1, 1.6 that of Tocomin® 50% in Tricaprylin for $\delta$-, $\gamma$- and $\alpha$-tocotrienols. Thus, in this part of the study, it is clearly shown that palm olein and soybean oil as a vehicle for tocotrienols can increase their absorption significantly.

In the second part of the study, different surfactant systems at various ratio were tried out to get a self-emulsifying drug delivery system (SEDDS). The aim of this part of the study is to incorporate tocotrienols into a suitable surfactant system that will cause the preparation (tocotrienols in oil vehicles) to self-emulsify/form an emulsion easily with gentle agitation, such as movement of the stomach/intestine. Different types of SEDDS which were tried out include the following system (i) Tween 85—Medium chain triglycerides (MCT)

(ii) Tween 80—Span 80—Palm olein (iii) Labrasol—Tween 80—Palm olein/Soybean oil

SEDDS are formulated in the absence of water by mixing oil with a non-ionic surfactant, a lipid base and a lipid soluble drug, in this case tocotrienols to form an isotropic oily solution. Upon dilution with water or in vivo administration, they formed fine oil in water emulsions. Labrasol-Tween 80-Palm olein/Soybean oil was found to be the best system due to the following reason:

(i) it can it can incorporate a bigger amount of tocotrienols without compensating the emulsification properties compared to the other two systems;

(ii) from the first part of the study, it was found that the absorption of tocotrienols from medium chain triglycerides was less than that of palm olein. Thus, the usage of Tween 85-medium chain triglycerides was not desirable; and (iii) between Tween 80-Span 80-Palm olein and Labrasol-Tween 80-Palm olein, the latter has a faster rate of emulsification and stability.

In accord with the present invention, the final master formulation is as follows:

| Ingredients | Weight per capsule (mg) |
|---|---|
| Tocomin ®50% | 148.66 |
| Palm olein/soybean oil | 351.34 |
| Labrasol | 87.00 |
| Tween 80 | 13.00 |
| Total weight | 600.00 |

The range of the oil to surfactant ratio were ±10% of the final formula. The ratio of the oil to surfactant was kept at 5 to 1 to avoid solubilization. Above the critical micellar concentration of a surfactant system, micellar complexation of tocotrienols might occur. It has been known that absorption of a drug incorporated in the micelle is negligible. Since the drug in the micellar phase.is unavailable for.absorption, the effective concentration of the drug is less than the apparent concentration, and a decreased absorption rate is observed (Gibaldi and Feldman, 1970, J. Pharm. Sci., 59:579–589).

Tocomin® 50% is mixed with palm olein and Labrasol is mixed with Tween 80 until homogenus. The mixing of the surfactant mixtures and the oil mixtures follows this. The final mixture was mixed until homogenous before filling it in soft gelatin capsules.

In the third part, a comparative in vivo bioavailability study was conducted to investigate the bioavailability of tocotrienols in the novel formulation with that of the conventional preparation at the dosage level of 200 mg tocotrienols. The novel formulation comprised Tocotrienols, Palm olein, Labrasol and Tween 80 at the ratio stated above in the master formula. The normal conventional preparation comprised tocotrienols and soybean oil. Both products are in the form of soft gelatin capsule.

Twelve (12) healthy adult male volunteers participated in a standard 2 period, 2-sequence crossover study after providing written informed consent. The volunteers were randomly divided into 2 groups of 6 each, and administered the preparations according to the schedule shown below:

| | Period | |
|---|---|---|
| Group | I | II |
| 1 | Conventional formulation | Novel formulation(X) |
| 2 | Novel formulation(X) | Conventional formulation |

On the first trial period, each volunteer in group 1 was given 4 capsules of conventional formulation (Y), while those of group 2, 4 capsules of novel formulation (X) containing an equivalent dose of tocotrienols. After a wash-out period of one week, each volunteer then received the alternate product. All products were administered in the morning (10:00 am) after an overnight fast with 240 ml of water. Food and drinks were withheld for at least 4 hours after dosing and plain water was given ad. libitum. Lunch and dinner comprising chicken with rice were served at 4 hours and 10 hours after dosing. Blood samples of 5-ml volume were collected in vacutainers (containing sodium heparin as anticoagulant) at 0 (before dosing), 1, 2, 3, 4, 5, 6, 7, 8, 10, 12, 14, 18, 24 hours after dosing via an in-dwelling cannula placed in the forearm. The blood samples were centrifuged for 15 min at 2000 G and the plasma transferred to separate glass containers to be kept frozen until analysis.

The protocol for the study was approved by a joint School of Pharmaceutical Sciences, USM-General Hospital Penang Committee on Bioavailability Studies. Volunteers were given information of the drug and nature of the study in advance of the trial.

Plasma levels of α-, γ- and δ-tocotrienols were analysed using a reversed-phase high performance liquid chromatography method reported by Yap et al (1999, Journal of Chromatography B, 735: 279–283).

The mean plasma δ-, γ- and α-tocotrienols concentration versus time profiles of the conventional preparation and the novel formulation are shown in FIGS. 2a, 2b and 2c. It is apparent from the plots that the profiles of the novel formulation were markedly higher than those of the conventional preparation for the three homologues of tocotrienols. Also, absorption from the novel formulation appeared to commence earlier than the conventional preparation. In addition, δ- and γ-tocotrienols were not detected in a number of individuals given the conventional preparation (3 subjects for δ-tocotrienol and 1 subject for γ-tocotrienol). In comparison, both tocotrienols were detectable in all subjects give the novel formulation, indicating better absorption from this formulation.

There was a statistically significant difference between the logarithmic transformed $AUC_{0-}$ ($p<0.01$), as well as the logarithmic transformed $C_{max}$ ($p<0.01$) values for all the homologues of the two preparations.

In addition, from the 90% confidence interval for the ratio of the logarithmic transformed $AUC_{0-\infty}$ values, it was estimated that the average extent of the novel formulation (X) was 2.6, 2.9 and 3.0 times that of the conventional preparation (Y) for δ-, γ- and α-tocotrienols respectively. In the case of the parameter $T_{max}$, the novel formulation has smaller numerical values compared to the conventional preparation suggesting that the former had a more rapid onset/rate of drug absorption. There was a statistically significant difference between the $T_{max}$ values of the two preparations ($p<0.05$).

Based on the results of the above studies, it is concluded that the novel formulation achieved a marked increase in the extent of absorption of tocotrienols compared to the conventional preparation. Additionally, the novel formulation also showed a more rapid onset or rate of absorption.

While the preferred embodiments of the present invention have been described, it should be understood that various changes, adaptations and modifications may be made thereto. It should be understood, therefore, that the invention is not limited to details of the invention and that variations in such minor details will be apparent to one skilled in the art.

What is claimed is:

1. A self-emulsifying drug delivery composition for use with oral administration of fat-soluble drugs, said composition consisting essentially of:

a fat-soluble drug selected from the group consisting of tocotrienols, tocopherols, vitamins A, D or K, and β-carotene;

an oil selected from the group consisting of palm olein and soy bean oil; and a surfactant system comprised of a first component consisting of caprylocaproyl macrogolglycerides and a second component consisting of polyoxyethylene 20 sorbitan monooleate, wherein the weight ratio of said first component to said second component is between 9/1 and 7/3 wherein said composition enhances the absorption of said fat-soluble drug and the weight ratio of the fat-soluble drug and oil to the surfactant system is about 5/1.

2. The composition of claim 1, wherein the fat-soluble drug is tocotrienol.

3. The composition of claim 1, wherein the fat-soluble drug is about 24.8 weight percent of the composition, the oil is about 58.5 weight percent of the composition and the surfactant system is about 16.7 weight percent of the composition.

4. The composition of claim 1, wherein said composition is administered in the form of a soft gelatin capsule.

* * * * *